United States Patent
Hoffmann et al.

(10) Patent No.: US 7,211,673 B2
(45) Date of Patent: May 1, 2007

(54) 4-TRIFLUOROMETHYLPYRAZOLYL-SUBSTITUTED PYRIDINES AND PYRIMIDINES

(75) Inventors: Michael G. Hoffmann, Florsheim (DE); Hendrik Helmke, Liederbach (DE); Lothar Willms, Hofheim (DE); Thomas Auler, Bad Soden (DE); Hermann Bieringer, Eppstein (DE); Hubert Menne, Hofheim (DE)

(73) Assignee: Bayer CropScience GmbH, Frankfurt (DE)

(*) Notice: Subject to any disclaimer, the term of this patent is extended or adjusted under 35 U.S.C. 154(b) by 0 days.

(21) Appl. No.: 11/325,957

(22) Filed: Jan. 5, 2006

(65) Prior Publication Data

US 2006/0122063 A1    Jun. 8, 2006

Related U.S. Application Data

(63) Continuation of application No. 10/627,573, filed on Jul. 24, 2003, now Pat. No. 7,022,650.

(30) Foreign Application Priority Data

Jul. 25, 2002   (DE) .................. 102 34 875

(51) Int. Cl.
    *C07D 409/14* (2006.01)
    *A01N 43/76* (2006.01)

(52) U.S. Cl. ................. 546/275.4

(58) Field of Classification Search ........... 546/256, 546/268.7, 269.1, 269.7, 271.1, 275.4, 272.1; 544/319, 320; 504/242, 250, 253
See application file for complete search history.

(56) References Cited

U.S. PATENT DOCUMENTS 5,750,470 A    5/1998  Morimoto et al.

6,448,204 B1    9/2002  Maier et al.
7,022,650 B2 *  4/2006  Hoffmann et al. .......... 504/242
2004/0198609 A1  10/2004  Hoffmann et al.
2004/0198758 A1  10/2004  Rapado et al.

FOREIGN PATENT DOCUMENTS

| EP | 1 101 764 A1 | 5/2001 |
| WO | WO-98/40379 | 9/1998 |
| WO | WO-99/28301 | 6/1999 |
| WO | WO-03/016308 A1 | 2/2003 |
| WO | WO-03/022843 | 3/2003 |

OTHER PUBLICATIONS

Selby et al., CAPLUS Abstract 136:200158, 2001.*

* cited by examiner

*Primary Examiner*—Deepak Rao
(74) *Attorney, Agent, or Firm*—Connolly Bove Lodge & Hutz LLP

(57) ABSTRACT

A description is given of 4-trifluoromethylpyrazolyl-substituted pyridines and pyrimidines of formula (I) and of their use as herbicides.

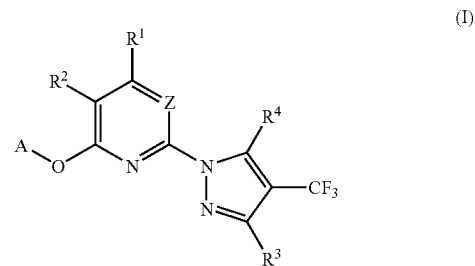

In this formula (I) $R^1$, $R^2$, $R^3$ and $R^4$ are various radicals, A is an aromatic or heteroaromatic radical, and Z is a nitrogen or carbon atom.

3 Claims, No Drawings

4-TRIFLUOROMETHYLPYRAZOLYL-SUBSTITUTED PYRIDINES AND PYRIMIDINES

CROSS REFERENCE TO RELATED APPLICATION

This application is a continuation of U.S. patent application Ser. No. 10/627,573 filed Jul. 24, 2003 (now U.S. Pat. No. 7,022,650).

The invention pertains to the technical field of herbicides, particularly that of herbicides from the class of the heteroaryl-pyrazoles, for selectively controlling broadleaf and gramineous weeds in crops of useful plants.

From a variety of publications it is already known that certain pyridines and pyrimidines substituted by azole radicals, such as pyrazolyl, imidazolyl, and triazolyl, possess herbicidal properties. For instance, WO 99/28301 discloses pyridines and pyrimidines which carry an azole radical in position 2 and, in position 6, an aromatic or heteroaromatic radical attached via a carbon atom. WO 98/40379 describes pyridines and pyrimidines which carry an azole radical in position 2 and, in position 6, an aromatic or heteroaromatic radical attached via an atom from the group consisting of oxygen, nitrogen, and sulfur. The azole radical in position 2 can be substituted by a variety of radicals. That publication discloses various substituents for the pyrazolyl radical, all of which are in position 3. EP-A 1 101 764 describes herbicidal pyridines substituted in position 2 by 3-trifluoromethyl-1-pyrazolyl.

WO 03/016308 describes 2-heterocyclyl-4-thienyloxy-pyrimidines.

The compounds known from these publications, however, frequently exhibit a herbicidal activity which is inadequate. It is an object of the present invention, therefore, to provide herbicidally effective compounds having herbicidal properties which are improved over those of the prior art compounds.

It has now been found that certain 4-trifluoromethylpyrazolyl-substituted pyridines and pyrimidines are particularly suitable herbicides. The present invention accordingly first provides compounds of the formula (I), their N-oxides, and their salts,

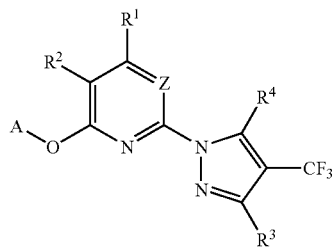

(I)

in which the radicals and indices have the following definitions:

Z is N or $CR^8$;
A is a radical from the group A6 to A15:

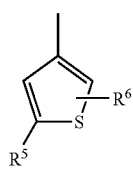

A6

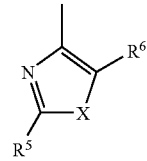

A7

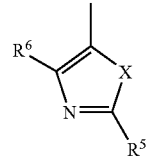

A8

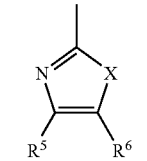

A9

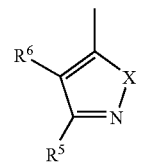

A10

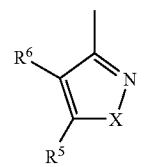

A11

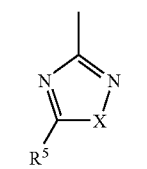

A12

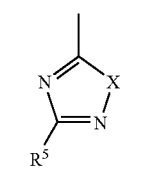

A13

A14

A15

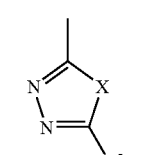

$R^1$ and $R^2$ independently are each hydrogen, halogen, cyano, isocyano, OH, $COOR^{10}$, $COR^{10}$, $CH_2OH$, $CH_2SH$, $CH_2NH_2$, $NO_2$, $(C_1-C_4)$-alkyl, halo-$(C_1-C_4)$-alkyl, $(C_3-C_6)$-cycloalkyl, $(C_1-C_4)$-alkoxy, halogen-$(C_1-C_4)$-alkoxy, $(C_1-C_2)$-alkoxy-$(C_1-C_2)$-alkyl, $(C_2-C_4)$-alkenyl, $(C_2-C_4)$-alkynyl, $(C_3-C_4)$-alkenyloxy, $(C_3-C_4)$-alkynyloxy, $(C_1-C_2)$-alkylthio-$(C_1-C_2)$-alkyl, $S(O)_nR^9$, $(C_1-C_2)$-alkylsulfonyl-$(C_1-C_2)$-alkyl, $NH_2$, $(C_1-C_4)$-alkyl-NH, $(C_1-C_3)$-alkyl-CO—NH, $(C_1-C_4)$-alkyl-$SO_2NH$ or di-$(C_1-C_4)$-alkylamino;

$R^3$ and $R^4$ independently are each hydrogen, halogen, cyano, $(C_1-C_4)$-alkyl, halo-$(C_1-C_4)$-alkyl, $(C_1-C_4)$-alkoxy or halo-$(C_1-C_4)$-alkoxy;

$R^5$ is halogen, cyano, $(C_1-C_4)$-alkyl, halo-$(C_1-C_4)$-alkyl, $(C_1-C_4)$-alkoxy, halo-$(C_1-C_4)$-alkoxy, halo-$(C_1-C_4)$-alkylthio, $(C_3-C_5)$-cycloalkyl, halo-$(C_3-C_5)$-cycloalkyl, $SF_5$, $S(O)_nR^9$, $(C_2-C_4)$-alkenyl or $(C_2-C_4)$-alkynyl;

$R^6$ is hydrogen, halogen, cyano, $(C_1-C_4)$-alkyl, halo-$(C_1-C_4)$-alkyl, $(C_1-C_4)$-alkoxy, halo-$(C_1-C_4)$-alkoxy or $S(O)_nR^9$;

$R^8$ is hydrogen, halogen, cyano, $(C_1-C_4)$-alkyl, $(C_1-C_4)$-alkoxy, hydroxy, amino, $(C_1-C_4)$-alkylamino, $(C_1-C_3)$-alkylcarbonylamino, $(C_1-C_4)$-alkylsulfonylamino, di-$(C_1-C_4)$-alkylamino or $S(O)_nR^9$;

$R^9$ is hydrogen, $(C_1-C_4)$-alkyl or halo-$(C_1-C_4)$-alkyl;

$R^{10}$ is hydrogen or $(C_1-C_4)$-alkyl;

X is oxygen or sulfur;

n is 0, 1 or 2.

In formula (I) and all subsequent formulae alkyl, alkenyl, and alkynyl radicals having more than two or, respectively, three carbon atoms can be straight-chain or branched. Alkyl radicals are methyl, ethyl, n- or i-propyl, n-, i-, t- or 2-butyl. Alkenyl accordingly is ethenyl, 1-propenyl, 2-propenyl, and the various butenyl isomers. Alkynyl is ethynyl, 1-propynyl, 2-propynyl, and the various butynyl isomers. The terms in their composite definitions, such as alkoxy, alkenyloxy, alkynyloxy, and alkylthio, are to be understood analogously. Thus alkynyloxy for example is $HC{\equiv}CCH_2O$, $CH_3C{\equiv}CCH_2O$ and $CH_3C{\equiv}CCH_2CH_2O$.

Cycloalkyl is cyclopropyl, cyclobutyl, cyclopentyl or cyclohexyl.

In the case of a doubly substituted amino group, such as dialkylamino, these two substituents can be identical or different.

Halogen is fluorine, chlorine, bromine or iodine. Haloalkyl is alkyl partly or fully substituted by halogen, preferably by fluorine, chlorine and/or bromine, in particular by fluorine or chlorine, e.g., $CF_3$, $CHF_2$, $CH_2F$, $CF_3CF_2$, $CH_2FCHCl$, $CCl_3$, $CHCl_2$, $CH_2CH_2Cl$; haloalkoxy is for example $OCF_3$, $OCHF_2$, $OCH_2F$, $CF_3CF_2O$, $OCH_2CF_3$, and $OCH_2CH_2Cl$; similar comments apply to other halogen-substituted radicals.

Depending on the nature and linking of the substituents the compounds of the formula (I) can exist as stereoisomers. Where there is double bond, for example, diastereomers may occur. Where, for example, there are one or more asymmetric carbon atoms, enantiomers and diastereomers may occur. Stereoisomers can be obtained from the as-prepared mixtures by standard separation methods, for example, by chromatographic separation techniques. Similarly, stereoisomers may be prepared selectively using stereoselective reactions and optically active starting materials and/or auxiliaries. The invention also relates to all of the stereoisomers and mixtures thereof which, while embraced by the formula (I), have not been specifically defined.

Compounds of the formula (I) may in principle form N-oxides. N-Oxides can be prepared in accordance with methods known to the skilled worker by reaction with oxidizing reagents such as peracids, hydrogen peroxide, and sodium perborate. Such methods are described for example in T. L. Gilchrist, Comprehensive Organic Synthesis, Volume 7, pages 748 to 750, S. V. Ley, Ed., Pergamon Press.

Compounds of the formula (I) can in principle form salts by addition with a) acids such as hydrogen chloride, hydrogen bromide, nitric acid, phosphoric acid, sulfuric acid, acetic acid, oxalic acid, or b) bases such as pyridine, ammonia, triethylamine, sodium carbonate, potassium carbonate, sodium hydroxide, potassium hydroxide.

Preferred embodiments of the compounds of the invention always include the N-oxides and salts, unless noted otherwise below.

Of particular interest are compounds of the formula (I) wherein Z is $CR^8$, and the other substituents and indices are each as defined earlier on above.

Compounds of the formula (I) which have been found advantageous are those wherein $R^3$ and $R^4$ independently are each hydrogen, halogen, methyl, methoxy or trifluoromethyl, and the other substituents and indices are each as defined earlier on above.

Preference is given to compounds of the formula (I) wherein $R^1$ is hydrogen, halogen, methoxy, methyl or ethyl, and $R^2$ is hydrogen, methyl, ethyl, methoxy, ethoxy, cyano, ethynyl, vinyl or formyl, and the other substituents and indices are each as defined earlier on above.

Preference is also given to compounds of the formula (I) wherein $R^3$ and $R^4$ are each hydrogen or methyl, and the other substituents and indices are each as defined earlier on above.

Particular preference is given to compounds of the formula (I) wherein $R^8$ is hydrogen, halogen or $(C_1-C_4)$-alkyl, and the other substituents and indices are each as defined earlier on above.

Likewise particularly preferred are compounds of the formula (I) wherein $R^5$ is halogen, cyano, halo-$(C_1-C_4)$-alkyl, halo-$(C_1-C_4)$-alkoxy or halo-$(C_1-C_4)$-alkylthio, and the other substituents and indices are each as defined earlier on above.

Additionally of particular preference are compounds of the formula (I) wherein $R^6$ is hydrogen or methyl, and the other substituents and indices are each as defined earlier on above.

Very particular preference is given to compounds of the formula (I) wherein

A is A6;

Z is N;

$R^1$ is hydrogen;

$R^2$ is hydrogen, methyl or ethyl;

$R^3$ is methyl or ethyl;

$R^4$ is hydrogen;

$R^5$ is trifluoromethyl;

$R^6$ is hydrogen, and the other substituents and indices are each as defined earlier on above.

In all formulae below the substituents and symbols have the same definition as described under formula (I) unless otherwise defined.

Compounds of the invention can be prepared for example by the reaction pathways indicated in the following schemes:

According to scheme 1 compounds of the formula (IIa) in which $E^1$ is a leaving group such as halogen, methylsulfonyl or tosyl are reacted under base catalysis with a compound of the formula (III). Such reactions are known to the skilled worker.

Scheme 1:

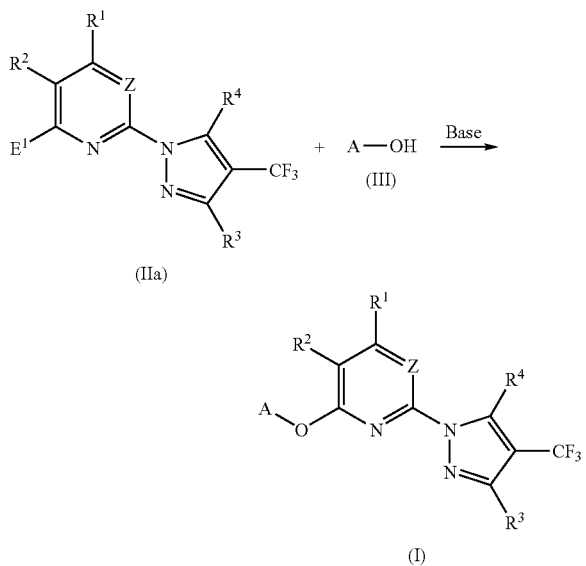

Compounds of the formula (IIa) in which $E^1$ is halogen can be prepared for example by scheme 2 under base catalysis from a compound of the formula (IV) in which $E^2$ is likewise a leaving group with a pyrazole of the formula (V). In this reaction the regioisomers (IIa) and (IIb) may be formed, and can be separated, for example, by chromatographic workup. Such reactions are known to the skilled worker.

Scheme 2:

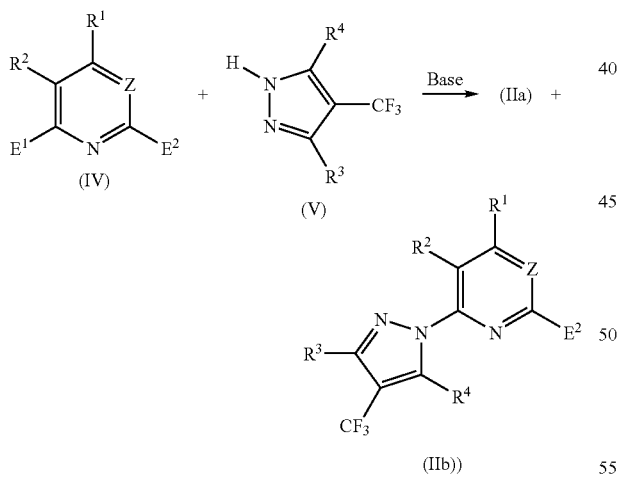

Compounds of the formula (IIa-2) in which $E^1$ is methylsulfonyl can be prepared, for example, in accordance with scheme 3 by oxidation with m-chloroperbenzoic acid (MCPA) or Oxone® from a compound of the formula (IIa-1). Such reactions are known to the skilled worker from, for example, J. March, *Advanced Organic Chemistry*, John Wiley, New York, 1992, 4th Ed., pages 1201 to 1203.

Pyrazoles of the formula (V) can be prepared in accordance with methods which are known to the skilled worker. The preparation of 4-trifluoromethylpyrazole, for example, is described in THL, 37, 11, 1996 pages 1829–1832.

The compounds of the formula (I) according to the invention have an excellent herbicidal activity against a broad range of economically important monocotyledonous and dicotyledonous weed plants. The active substances control perennial weeds equally well which produce shoots from rhizomes, root stocks or other perennial organs and which cannot be easily controlled. In this context, it generally does not matter whether the substances are applied before sowing, pre-emergence or post-emergence. Some representatives of the monocotyledonous and dicotyledonous weed flora which can be controlled by the compounds according to the invention may be mentioned individually as examples, but this is not to be taken to mean a restriction to certain species. The monocotyledonous weed species which are controlled well are, for example, *Avena, Lolium, Alopecurus, Phalaris, Echinochloa, Digitaria, Setaria* and *Cyperus* species from the annual group, and *Agropyron, Cynodon, Imperata* and *Sorghum* or else perennial *Cyperus* species amongst the perennial species. In the case of dicotyledonous weed species, the spectrum of action extends to species such as, for example, *Galium, Viola, Veronica, Lamium, Stellaria, Amaranthus, Sinapis, Ipomoea, Sida, Matricaria* and *Abutilon* from the annual group, and *Convolvulus, Cirsium, Rumex* and *Artemisia* among the perennials. Weed plants which are found under the specific culture conditions of rice, such as, for example, *Echinochloa, Sagittaria, Alisma, Eleocharis, Scirpus* and *Cyperus*, are also controlled outstandingly well by the active substances according to the invention. If the compounds according to the invention are applied to the soil surface prior to germination, then either emergence of the weed seedlings is prevented completely, or the weeds grow until they have reached the cotyledon stage but growth then comes to a standstill and, after a period of three to four weeks, the plants eventually die completely. When the active substances are applied post-emergence to the green parts of the plants, growth also stops drastically very soon after the treatment, and the weeds remain at the growth stage of the time of application, or, after a certain period of time, they die completely so that competition Scheme 3:

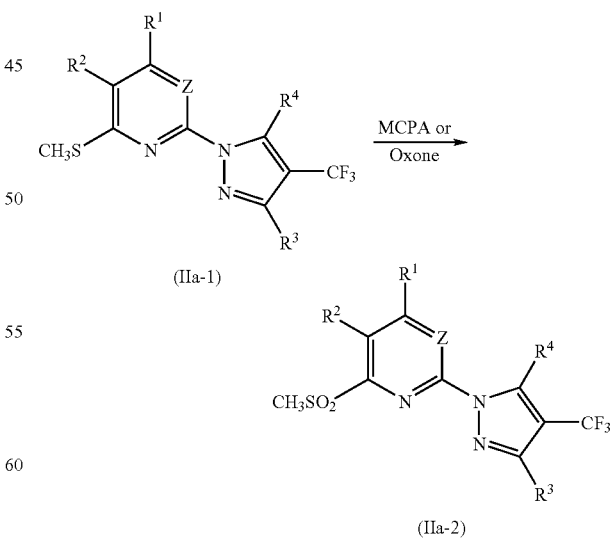

Compounds of the formula (IIa-1) can be prepared for example in accordance with scheme 4 by base-catalyzed reaction of a compound of the formula (VI) with a pyrazole (V). Suitable bases include the carbonates of potassium and sodium, the hydroxides of potassium and sodium, and sodium hydride. Such reactions are known to the skilled worker.

Scheme 4:

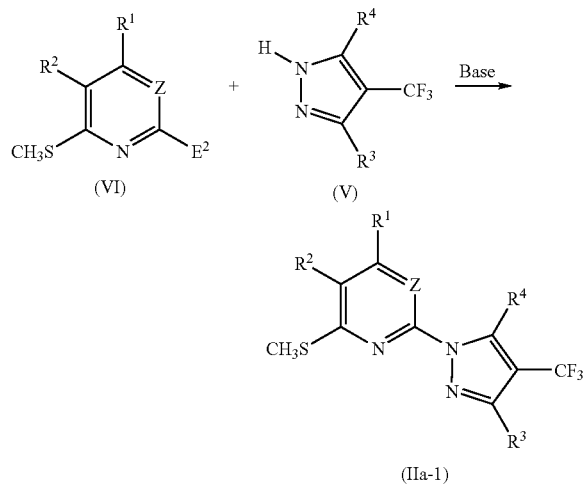

Compounds of the formula (VI) can be prepared for example from compounds of the formula (IV) in which $E^1$ and $E^2$ are each halogen by reaction with a sodium salt or potassium salt of methyl mercaptan in tetrahydrofuran or dioxane. Such reactions are known to the skilled worker.

Compounds of the formula (IV) in which $E^1$ and $E^2$ are each halogen are either available commercially or can be prepared in accordance with methods known to the skilled worker. Methods of this kind known to the skilled worker are described for example in *Advances in Heterocyclic Chemistry*, Katritzky, A. R., Ed., Academic Press, New York, 1993, Volume 58, pages 301 to 305; *Heterocyclic Compounds*, Elderfield, R. C., Ed., John Wiley, New York, 1957, Volume 6, pages 265 to 270. by the weeds, which is detrimental for the crop plants, is thus eliminated at a very early stage and in a sustained manner. In particular, the compounds according to the invention have an outstanding action against *Amaranthus retroflexus, Avena* sp., *Echinochloa* sp., *Cyperus serotinus, Lolium multiflorum, Setaria viridis, Sagittaria pygmaea, Scirpus juncoides, Sinapis* sp. and *Stellaria media*.

Although the compounds according to the invention have an outstanding herbicidal activity against monocotyledonous and dicotyledonous weeds, crop plants of economically important crops such as, for example, wheat, barley, rye, rice, maize, sugar beet, cotton and soya, only suffer negligible damage, if any. In particular, they are outstandingly well tolerated in wheat, maize, rice, and soybean. This is why the present compounds are highly suitable for the selective control of unwanted vegetation in stands of agricultural useful plants or of ornamentals.

Owing to their herbicidal properties, the active substances can also be employed for controlling weed plants in crops of known plants or genetically modified plants which are yet to be developed. As a rule, the transgenic plants are distinguished by particularly advantageous properties, for example by resistances to certain pesticides, especially certain herbicides, by resistances to plant diseases or causative organisms of plant diseases, such as certain insects or microorganisms such as fungi, bacteria or viruses. Other particular properties concern for example the harvested material with regard to quantity, quality, storage properties, composition and specific constituents. Thus, transgenic plants are known which have an increased starch content or whose starch quality has been modified, or those whose fatty acid composition in the harvested material is different.

The compounds of the formula (I) according to the invention or their salts are preferably employed in economically important transgenic crops of useful plants and ornamentals, for example cereals such as wheat, barley, rye, oats, millet, rice, cassava and maize, or else crops of sugar beet, cotton, soya, oilseed rape, potato, tomato, pea and other vegetables. The compounds of the formula (I) can preferably be employed as herbicides in crops of useful plants which are resistant, or have been genetically modified to be resistant, to the phytotoxic effects of the herbicides.

Conventional routes for the generation of novel plants which have modified properties compared with existing plants are, for example, traditional breeding methods and the generation of mutants. Alternatively, novel plants with modified properties can be generated with the aid of recombinant methods (see, for example, EP-A-0221044, EP-A-0131624). For example, several cases of the following have been described:

recombinant modifications of crop plants for the purposes of modifying the starch synthesized in the plants (for example WO 92/11376, WO 92/14827, WO 91/19806), transgenic crop plants which exhibit resistances to certain herbicides of the glufosinate type (cf. eg. EP-A-0242236, EP-A-242246), glyphosate type (WO 92/00377) or of the sulfonylurea type (EP-A-0257993, U.S. Pat. No. 5,013,659)

transgenic crop plants, for example cotton, with the ability to produce *Bacillus thuringiensis* toxins (Bt toxins), which make the plants resistant to certain pests (EP-A-0142924, EP-A-0193259), transgenic crop plants with a modified fatty acid spectrum (WO 91/13972), A large number of techniques in molecular biology, with the aid of which novel transgenic plants with modified properties can be generated, are known in principle; see, for example, Sambrook et al., 1989, Molecular Cloning, A Laboratory Manual, 2nd Ed., Cold Spring Harbor Laboratory Press, Cold Spring Harbor, N.Y.; or Winnacker "Gene und Klone" [Genes and Clones], VCH Weinheim 2nd Edition 1996 or Christou, "Trends in Plant Science" 1 (1996) 423–431.

To carry out such recombinant manipulations, nucleic acid molecules can be introduced into plasmids which permit a mutagenesis or a sequence alteration by recombination of DNA sequences. With the aid of the abovementioned standard methods, it is possible, for example, to carry out base substitutions, to remove part sequences or to add natural or synthetic sequences. The fragments can be provided with adapters or linkers to link the DNA fragments to each other.

Plant cells with a reduced activity of a gene product can be obtained, for example, by expressing at least one corresponding antisense RNA, a sense RNA for achieving a cosuppression effect, or the expression of at least one suitably constructed ribozyme which specifically cleaves transcripts of the abovementioned gene product.

To this end, it is possible, on the one hand, to use DNA molecules which encompass all of the coding sequence of a gene product including any flanking sequences which may be present, but also DNA molecules which only encompass portions of the coding sequence, it being necessary for these portions to be so long as to cause an antisense effect in the cells. Another possibility is the use of DNA sequences which have a high degree of homology with the coding sequences of a gene product, but are not completely identical.

In the expression of nucleic acid molecules in plants, the protein synthesized may be localized in any desired compartment of the plant cell. However, to achieve localization in a particular compartment, the coding region can, for example, be linked to DNA sequences which ensure localization in a particular compartment. Such sequences are known to the skilled worker (see, for example, Braun et al., EMBO J. 11 (1992), 3219–3227; Wolter et al., Proc. Natl. Acad. Sci. USA 85 (1988), 846–850; Sonnewald et al., Plant J. 1 (1991), 95–106).

The transgenic plant cells can be regenerated by known techniques to give intact plants. In principle, the transgenic plants can be plants of any desired plant species, i.e. both monocotyledonous and dicotyledonous plants.

Thus, transgenic plants can be obtained which exhibit modified properties owing to the overexpression, suppression or inhibition of homologous (i.e. natural) genes or gene sequences or expression of heterologous (i.e. foreign) genes or gene sequences.

When using the active substances according to the invention in transgenic crops, effects are frequently observed in addition to the effects against weed plants to be observed in other crops, which are specific for the application in the transgenic crop in question, for example a modified or specifically widened weed spectrum which can be controlled, modified application rates which may be employed for the application, preferably good combining ability with the herbicides to which the transgenic crop is resistant, and an effect on the growth and yield of the transgenic crop plants. The invention therefore also provides for the use of the compounds according to the invention as herbicides for controlling weed plants in transgenic crop plants. The substances according to the invention additionally have outstanding growth-regulatory properties in crop plants. They intervene in the plants' metabolism in a regulatory fashion and can thus be employed for the targeted control of plant constituents and for facilitating harvesting, such as, for example, triggering desiccation and stunted growth. Moreover, they are also suitable for generally controlling and inhibiting unwanted vegetative growth without destroying the plants in the process. Inhibiting the vegetative growth plays an important role in many monocotyledonous and dicotyledonous crops, allowing lodging to be reduced or prevented completely.

The compounds according to the invention can be employed in the form of wettable powders, emulsifiable concentrates, sprayable solutions, dusts or granules in the customary preparations. The invention therefore furthermore relates to herbicidal compositions comprising compounds of the formula (I). The compounds of the formula (I) can be formulated in various ways, depending on the prevailing biological and/or chemico-physical parameters. Examples of suitable formulations which are possible are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), seed-dressing products, granules for spreading and soil application, granules (GR) in the form of microgranules, spray granules, coated granules and adsorption granules, water-dispersible granules (WG), water-soluble granules (SG), ULV formulations, microcapsules and waxes. These individual formulation types are known in principle and are described, for example, in Winnacker-Küchler, "Chemische Technologie" [Chemical Technology], Volume 7, C. Hauser Verlag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and further additives, are likewise known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie", Volume 7, C. Hauser Verlag Munich, 4th Ed. 1986.

Wettable powders are preparations which are uniformly dispersible in water and which, in addition to the active substance, also contain ionic and/or nonionic surfactants (wetters, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium 2,2'-dinaphthylmethane-6,6'-disulfonate, sodium lignosulfonate, sodium dibutyinaphthalenesulfonate or else sodium oleoylmethyltaurate, in addition to a diluent or inert substance. To prepare the wettable powders, the herbicidal active substances are ground finely, for example in customary equipment such as hammer mills, blowing mills and air-jet mills, and simultaneously or subsequently mixed with the formulation auxiliaries.

Emulsifiable concentrates are prepared by dissolving the active substance in an organic solvent, such as butanol, cyclohexanone, dimethylformamide, xylene or else higher-boiling aromatics or hydrocarbons or mixtures of the organic solvents with addition of one or more ionic and/or nonionic surfactants (emulsifiers). Examples of emulsifiers which can be used are: calcium alkylarylsulfonate salts such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan esters such as, for example, sorbitan fatty acid esters or polyoxyethylene sorbitan esters such as, for example, polyoxyethylene sorbitan fatty acid esters.

Dusts are obtained by grinding the active substance with finely divided solid materials, for example talc, natural clays, such as kaolin, bentonite and pyrophyllite, or diatomaceous earth.

Suspension concentrates can be water based or oil based. They can be prepared for example by wet grinding by means of customary bead mills, if appropriate with addition of surfactants, as have already been mentioned for example above in the case of the other formulation types.

Emulsions, for example oil-in-water emulsions (EW), can be prepared for example by means of stirrers, colloid mills and/or static mixers using aqueous organic solvents and, if appropriate, surfactants as have already been mentioned for example above in the case of the other formulation types.

Granules can be prepared either by spraying the active substance onto adsorptive, granulated inert material or by applying active substance concentrates to the surface of carriers such as sand, kaolinites or granulated inert material with the aid of stickers, for example polyvinyl alcohol, sodium polyacrylate or else mineral oils. Suitable active substances can also be granulated in the fashion which is conventional for the production of fertilizer granules, if desired as a mixture with fertilizers.

Water-dispersible granules are generally prepared by customary methods such as spray drying, fluidized-bed granulation, disk granulation, mixing with high-speed stirrers and extrusion without solid inert material.

To prepare disk granules, fluidized-bed granules, extruder granules and spray granules see, for example, methods in "Spray-Drying Handbook" 3rd Ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, pp. 8–57.

For further details on the formulation of crop protection products see, for example, G. C. Klingman, "Weed Control as a Science", John Wiley and Sons, Inc., New York, 1961, pages 81–96 and J. D. Freyer, S. A. Evans, "Weed Control Handbook", 5th Ed., Blackwell Scientific Publications, Oxford, 1968, pages 101–103.

As a rule, the agrochemical preparations comprise 0.1 to 99% by weight, in particular 0.1 to 95% by weight, of active substance of the formula (I). In wettable powders, the active substance concentration is, for example, approximately 10 to 90% by weight, the remainder to 100% by weight being composed of customary formulation constituents. In the case of emulsifiable concentrates, the active substance concentration can amount to approximately 1 to 90, preferably 5 to 80% by weight. Formulations in the form of dusts comprise 1 to 30% by weight of active substance, preferably in most cases 5 to 20% by weight of active substance, and sprayable solutions comprise approximately 0.05 to 80, preferably 2 to 50% by weight of active substance. In the case of water-dispersible granules, the active substance content depends partly on whether the active compound is in liquid or solid form and on the granulation auxiliaries, fillers and the like which are being used. In the case of the water-dispersible granules, for example, the active substance content is between 1 and 95% by weight, preferably between 10 and 80% by weight.

In addition, the active substance formulations mentioned comprise, if appropriate, the tackifiers, wetters, dispersants, emulsifiers, penetrants, preservatives, antifreeze agents, solvents, fillers, carriers, colorants, antifoams, evaporation inhibitors, and pH and viscosity regulators which are conventional in each case.

Based on these formulations, it is also possible to prepare combinations with other pesticidally active substances such as, for example, insecticides, acaricides, herbicides, fungicides, and with safeners, fertilizers and/or growth regulators, for example in the form of a readymix or a tank mix.

Active substances which can be employed in combination with the active substances according to the invention in mixed formulations or in the tank mix are, for example, known active substances as are described, for example, in Weed Research 26, 441–445 (1986) or "The Pesticide Manual", 11th edition, The British Crop Protection Council and the Royal Soc. of Chemistry, 1997 and literature cited therein. Known herbicides which must be mentioned, and can be combined with the compounds of the formula (I), are, for example, the following active substances (note: the compounds are either designated by the common name according to the International Organization for Standardization (ISO) or using the chemical name, if appropriate together with a customary code number): acetochlor; acifluorfen; aclonifen; AKH 7088, i.e. [[[1-[5-[2-chloro-4-(trifluoromethyl)-phenoxy]-2-nitrophenyl]-2-methoxyethylidene]amino]oxy]acetic acid and its methyl ester; alachlor; alloxydim; ametryn; amidosulfuron; amitrol; AMS, i.e. ammonium sulfamate; anilofos; asulam; atrazine; azimsulfurone (DPX-A8947); aziprotryn; barban; BAS 516H, i.e. 5-fluoro-2-phenyl-4H-3,1-benzoxazin-4-one; benazolin; benfluralin; benfuresate; bensulfuronmethyl; bensulide; bentazone; benzofenap; benzofluor; benzoylprop-ethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; cafenstrole (CH-900); carbetamide; cafentrazone (ICI-A0051); CDAA, i.e. 2-chloro-N,N-di-2-propenylacetamide; CDEC, i.e. 2-chloroallyl diethyldithiocarbamate; chlomethoxyfen; chloramben; chlorazifop-butyl, chlormesulon (ICI-A0051); chlorbromuron; chlorbufam; chlorfenac; chlorflurecol-methyl; chloridazon; chlorimuron ethyl; chlornitrofen; chlorotoluron; chloroxuron; chlorpropham; chlorsulfuron; chlorthal-dimethyl; chlorthiamid; cinmethylin; cinosulfuron; clethodim; clodinafop and its ester derivatives (for example clodinafop-propargyl); clomazone; clomeprop; cloproxydim; clopyralid; cumyluron (JC 940); cyanazine; cycloate; cyclosulfamuron (AC 104); cycloxydim; cycluron; cyhalofop and its ester derivatives (for example butyl ester, DEH-112); cyperquat; cyprazine; cyprazole; daimuron; 2,4-DB; dalapon; desmedipham; desmetryn; di-allate; dicamba; dichlobenil; dichlorprop; diclofop and its esters such as diclofop-methyl; diethatyl; difenoxuron; difenzoquat; diflufenican; dimefuron; dimethachlor; dimethametryn; dimethenamid (SAN-582H); dimethazone, clomazon; dimethipin; dimetrasulfuron, dinitramine; dinoseb; dinoterb; diphenamid; dipropetryn; diquat; dithiopyr; diuron; DNOC; eglinazine-ethyl; EL 77, i.e. 5-cyano-1-(1,1-dimethylethyl)-N-methyl-1H-pyrazole-4-carboxamide; endothal; EPTC; esprocarb; ethalfluralin; ethametsulfuron-methyl; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl]phenyl]ethanesulfonamide; ethoxyfen and its esters (for example ethyl ester, HN-252); etobenzanid (HW 52); fenoprop; fenoxan, fenoxaprop and fenoxaprop-P and their esters, for example fenoxaprop-P-ethyl and fenoxaprop-ethyl; fenoxydim; fenuron; flamprop-methyl; flazasulfuron; fluazifop and fluazifop-P and their esters, for example fluazifop-butyl and fluazifop-P-butyl; fluchloralin; flumetsulam; flumeturon; flumiclorac and its esters (for example pentyl ester, S-23031); flumioxazin (S-482); flumipropyn; flupoxam (KNW-739); fluorodifen; fluoroglycofen-ethyl; flupropacil (UBIC-4243); fluridone; flurochloridone; fluroxypyr; flurtamone; fomesafen; fosamine; furyloxyfen; glufosinate; glyphosate; halosafen; halosulfuron and its esters (for example methylester, NC-319); haloxyfop and its esters; haloxyfop-P (=R-haloxyfop) and its esters; hexazinone; imazapyr; imazamethabenz-methyl; imazaquin and salts such as the ammonium salt; ioxynil; imazethamethapyr; imazethapyr; imazosulfuron; isocarbamid; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor; metham; methabenzthiazuron; methazole; methoxyphenone; methyldymron; metabenzuron, methobenzuron; metobromuron; metolachlor; metosulam (XRD 511); metoxuron; metribuzin; metsulfuron-methyl; MH; molinate; monalide; monolinuron; monuron; monocarbamide dihydrogensulfate; MT 128, i.e. 6-chloro-N-(3-chloro-2-propenyl)-5-methyl-N-phenyl-3-pyridazinamine; MT 5950, i.e. N-[3-chloro-4-(1-methylethyl)phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxyfluorfen; paraquat; pebulate; pendimethalin; perfluidone; phenisopham; phenmedipham; picloram; piperophos; piributicarb; pirifenop-butyl; pretilachlor; primisulfuron-methyl; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prosulfuron (CGA-152005); prynachlor; pyrazolinate; pyrazon; pyrazosulfuron-ethyl; pyrazoxyfen; pyridate; pyrithiobac (KIH-2031); pyroxofop and its esters (for example propargyl ester); quinclorac; quinmerac; quinofop and its ester derivatives; quizalofop and quizalofop-P and their ester derivatives for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyl]oxy]propanoic acid and its methyl ester; sulfentrazon (FMC-97285, F-6285); sulfazuron; sulfometuron-methyl; sulfosate (ICI-A0224); TCA; tebutam (GCP-5544); tebuthiuron; terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiazafluron; thiazopyr (Mon-13200); thidiazimin (SN-24085); thiobencarb; thifensulfuron-methyl; tiocarbazil; tralkoxydim; tri-allate; triasulfuron; triazofenamide; tribenuron-methyl; triclopyr; tridiphane; trietazine; trifluralin; triflusulfuron and esters (for example methyl ester, DPX-66037); trimeturon; tsitodef; vemolate; WL 110547, i.e. 5-phenoxy-1-[3-(trifluoromethyl)phenyl]-1H-tetrazole; UBH-509; D489; LS 82-556; KPP-300; NC-324; NC-330; KH-218; DPX-N8189; SC-0774; DOWCO-535; DK-8910; V-53482; PP-600; MBH-001; KIH-9201; ET-751; KIH-6127 and KIH-2023. For use, the formulations, which are present in commercially available form, are diluted in the customary manner, for example using water in the case of wettable powders, emulsifiable concentrates, dispersions and water-dispersible granules. Preparations in the form of dusts, soil granules, granules for spreading and sprayable solutions are usually not diluted any further with other inert substances prior to use. The application rate required of the compounds of the formula (I) varies with the external conditions such as, inter alia, temperature, humidity and the nature of the herbicide used. It can vary within wide limits, for example between 0.001 and 1.0 kg/ha or more of active substance, but it is preferably between 0.005 and 750 g/ha.

The examples which follow illustrate the invention.

A. CHEMICAL EXAMPLES

Preparation of 5-methyl-2-(4-trifluoromethyl-1H-1-pyrazolyl)-4-(5-trifluoromethyl-3-thienyloxy)pyrimidine A mixture of 0.8 g (2.6 mmol) of 5-methyl-4-methylsulfonyl-2-(4-trifluoromethyl-1H-1-pyrazolyl)pyrimidine, 0.44 g (2.6 mmol) of 3-hydroxy-5-trifluoromethylthiophene and 0.72 g (5.2 mmol) of $K_2CO_3$ in 10 ml of DMF is stirred at 60° C. for 6 h and then at RT for 48 h. It is subsequently poured into 20 ml of water and extracted with four times 15 ml of $CH_2Cl_2$. The combined organic phase is dried over $Na_2SO_4$, filtered and concentrated. Chromatographic purification on silica gel with heptane/ethyl acetate (3:7) as eluent gives 0.5 g of 5-methyl-2-(4-trifluoromethyl-1H-1-pyrazolyl)-4-(5-trifluoromethyl-3-thienyloxy)pyrimidine as colorless crystals.

$^1$H-NMR: δ [$CDCl_3$] 2.35 (s, 3H), 7.47 (s, 1H), 7.58 (s, 1H), 8.55 (s, 1H), 8.48 (s, 1H), 9.94 (s, 1H).

Preparation of 5-methoxy-2-(4-trifluoromethyl-1H-1-pyrazolyl)-4-(5-trifluoromethyl-3-thienyloxy)pyrimidine A mixture of 0.4 g (1.24 mmol) of 5-methoxy-4-methylsulfonyl-2-(4-trifluoromethyl-1H-1-pyrazolyl)pyrimidine, 0.27 g (1.60 mmol) of 3-hydroxy-5-trifluoromethylthiophene and 0.34 g (2.47 mmol) of $K_2CO_3$ in 10 ml of DMF is stirred at 60° C. for 6 h and then at RT for 48 h. It is subsequently poured into 20 ml of water and extracted with four times 15 ml of $CH_2Cl_2$. The combined organic phase is dried over $Na_2SO_4$, filtered and concentrated. Chromatographic purification on silica gel with heptane/ethyl acetate (3:7) as eluent gives 0.3 g of 5-methoxy-2-(4-trifluoromethyl-1H-1-pyrazolyl)-4-(5-trifluoromethyl-3-thienyloxy)pyrimidine as colorless crystals.

$^1$H-NMR: δ [$CDCl_3$] 4.06 (s, 3H), 7.49 (s, 1H), 7.57 (s, 1H), 7.96 (s, 1H), 8.48 (s, 1H), 8.26 (s, 1H)

Preparation of 2-fluoro-6-(2-trifluoromethyl-4-thienyloxy)pyridine 1.00 g of 2,6-difluoropyridine is introduced into 10 ml of DMF under nitrogen and 1.44 g of $K_2CO_3$ are added at RT. 1.61 g of 4-hydroxy-2-trifluoromethylthiophene are added and the mixture is heated at 80° C. for 4 h, then cooled to RT and poured into water. After extraction twice with heptane/ethyl acetate (1:1) and twice with ethyl acetate the product is washed with water and saturated sodium chloride solution, dried over $MgSO_4$ and concentrated. Chromatographic purification on silica gel with heptane/ethyl acetate (3:7) as eluent gives 1.7 g of 2-fluoro-6-(2-trifluoromethyl-4-thienyloxy)pyridine as a colorless oil.

$^1$H-NMR: δ [$CDCl_3$] 6.64 (dd, 1H), 6.64 (dd, 1H), 6.80 (dd, 1H), 7.30 (d, 1H), 7.78 (m, 1H)

Preparation of 2-(4-trifluoromethylpyrazol-1-yl)-6-(2-trifluormethyl-4-thienyloxy)pyridine 0.114 g of 4-trifluoromethylpyrazole is introduced in 5 ml of dimethylacetamide under nitrogen and at 0° C. 0.028 g of NaH is added. The mixture is allowed to come to RT over 30 min and then 0.2 g of 2-fluoro-6-(2-trifluormethyl-4-thienyloxy)pyridine is added and the mixture is heated at 80° C. for 9 h, cooled to RT and poured into water. After threefold extraction with ethyl acetate the product is washed with water and saturated sodium chloride solution, dried over $MgSO_4$ and concentrated. Chromatographic purification on silica gel with heptane/ethyl acetate (3:7) as eluent gives 0.043 g of 2-(4-trifluoromethylpyrazol-1-yl)-6-(2-trifluoromethyl-4-thienyloxy)pyridine as colorless crystals.

$^1$H-NMR: δ [$CDCl_3$] 6.90 (dd, 1H), 7.28 (dd, 1H), 7.43 (s, 1H), 7.77 (d, 1H), 7.88 (m, 2H), 8.46 (s, 1H).

The examples listed in tables below were prepared in analogy to methods specified above or are obtainable in analogy to the methods specified above.

The abbreviations used here have the following definitions:
Et=ethyl OEt=ethoxy Me=methyl
OMe=methoxy EE=ethyl ethanoate m.p.=melting point
Rt=retention value i-Pr=iso-propyl n-Pr=n-propyl

TABLE 1

Compounds of the formula (I) according to the invention in which the substituents and symbols are defined as follows:

A = A6        R⁶ = H

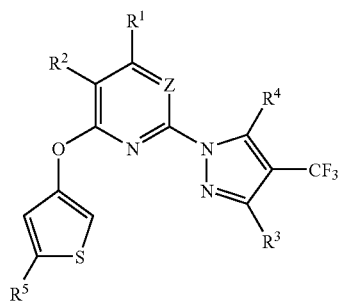

(Ia)

| No. | R¹ | R² | R³ | R⁴ | R⁵ | Z | Physical data |
|---|---|---|---|---|---|---|---|
| 1.1 | H | H | H | H | Cl | N | |
| 1.2 | H | H | Me | Me | F | N | |
| 1.3 | H | H | H | Me | CN | N | |
| 1.4 | H | H | H | H | CF$_3$ | CH | $^1$H-NMR: δ [CDCl$_3$] 6.90 (dd, 1H), 7.28 (dd, 1H), 7.43 (s, 1H), 7.77 (d, 1H), 7.88 (m, 2H), 8.46 (s, 1H), |
| 1.5 | H | H | Me | H | OCF$_3$ | CMe | |
| 1.6 | H | H | Me | Me | Br | CCl | |
| 1.7 | H | H | H | Me | OCF$_3$ | CF | |
| 1.8 | H | Me | H | H | CF$_3$ | N | m.p. 94–96° C. |
| 1.9 | H | Me | H | H | OCF$_2$H | N | |
| 1.10 | H | Me | H | Me | CN | N | |
| 1.11 | H | Me | H | H | Br | CH | |
| 1.12 | H | Me | Me | Me | OCF$_3$ | CMe | |
| 1.13 | H | Me | H | Me | CF$_3$ | CCl | |
| 1.14 | H | Me | Me | H | OCF$_2$H | CF | |
| 1.15 | H | Et | H | H | CF$_3$ | N | |
| 1.16 | H | Et | H | H | OCF$_2$H | N | |
| 1.17 | H | Et | H | Me | CN | N | |
| 1.18 | H | Et | H | H | Br | CH | |
| 1.19 | H | Et | Me | Me | OCF$_3$ | CMe | |
| 1.20 | H | Et | H | Me | CF$_3$ | CCl | |
| 1.21 | H | Et | Me | H | OCF$_2$H | CF | |
| 1.22 | H | OMe | H | H | CF$_3$ | N | m.p. 109–111° C. |
| 1.23 | H | OMe | H | Me | CN | N | |
| 1.24 | H | OMe | H | Me | CF$_3$ | N | |
| 1.25 | H | OMe | H | H | CF$_3$ | CH | |
| 1.26 | H | OMe | H | Me | CF$_3$ | CMe | |
| 1.27 | H | OEt | H | H | CF$_3$ | N | |
| 1.28 | H | OEt | H | Me | CF$_3$ | N | |
| 1.29 | H | OEt | H | Me | CF$_3$ | N | |
| 1.30 | H | OEt | Me | Me | CF$_3$ | CH | |
| 1.31 | H | OEt | H | Me | CH$_2$CF$_3$ | CMe | |
| 1.32 | H | CN | H | H | CH$_2$CF$_3$ | N | |
| 1.33 | H | CN | H | Me | CF$_3$ | N | |
| 1.34 | H | CN | Me | H | CF$_3$ | CH | |
| 1.35 | H | CN | H | H | CF$_3$ | CMe | |
| 1.36 | H | CHO | H | H | CH$_2$CF$_3$ | N | |
| 1.37 | H | CHO | H | Me | CF$_3$ | CH | |
| 1.38 | H | CHO | Me | H | CF$_3$ | N | |
| 1.39 | H | CHO | Me | Me | CF$_3$ | CMe | |
| 1.40 | H | Vinyl | H | H | CH$_2$CF$_3$ | N | |
| 1.41 | H | Vinyl | H | Me | CF$_3$ | CH | |
| 1.42 | H | Vinyl | Me | H | CF$_3$ | N | |
| 1.43 | H | Vinyl | Me | Me | CF$_3$ | CMe | |
| 1.44 | H | Ethynyl | H | H | CH$_2$CF$_3$ | N | |
| 1.45 | H | Ethynyl | H | Me | CF$_3$ | CH | |
| 1.46 | H | Ethynyl | Me | H | CF$_3$ | N | |
| 1.47 | H | Ethynyl | Me | Me | CF$_3$ | CMe | |
| 1.48 | Me | H | H | H | Cl | N | |
| 1.49 | Me | H | Me | Me | F | N | |
| 1.50 | Me | H | H | Me | CN | N | |
| 1.51 | Me | H | H | H | SCF$_3$ | CH | |
| 1.52 | Me | H | Me | H | OCF$_3$ | CMe | |

TABLE 1-continued

Compounds of the formula (I) according to the invention in which the substituents and symbols are defined as follows:

A = A6    $R^6$ = H

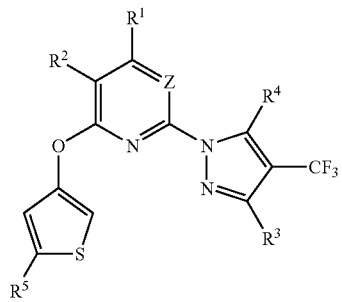

(Ia)

| No. | $R^1$ | $R^2$ | $R^3$ | $R^4$ | $R^5$ | Z | Physical data |
|---|---|---|---|---|---|---|---|
| 1.53 | Me | H | Me | Me | Br | CCl | |
| 1.54 | Me | H | H | Me | OCF$_3$ | CF | |
| 1.55 | Me | Me | H | H | CF$_3$ | N | |
| 1.56 | Me | Me | H | H | OCF$_2$H | N | |
| 1.57 | Me | Me | H | Me | CN | N | |
| 1.58 | Me | Me | Me | Me | Br | CH | |
| 1.59 | Me | Me | Me | Me | OCF$_3$ | CMe | |
| 1.60 | Me | Me | H | Me | CF$_3$ | CCl | |
| 1.61 | Me | Me | Me | H | OCF$_2$H | CF | |
| 1.62 | Me | Et | H | H | CF$_3$ | N | |
| 1.63 | Me | Et | H | H | OCF$_2$H | N | |
| 1.64 | Me | Et | H | Me | CN | N | |
| 1.65 | Me | Et | Me | Me | Br | CH | |
| 1.66 | Me | Et | Me | Me | OCF$_3$ | CMe | |
| 1.67 | Me | Et | H | Me | CF$_3$ | CCl | |
| 1.68 | Me | Et | Me | H | OCF$_2$H | CF | |
| 1.69 | Me | OMe | H | H | CF$_3$ | N | |
| 1.70 | Me | OMe | H | Me | CN | N | |
| 1.71 | Me | OMe | H | Me | CF$_3$ | N | |
| 1.72 | Me | OMe | Me | Me | CF$_3$ | CH | |
| 1.73 | Me | OMe | H | Me | CF$_3$ | CMe | |
| 1.74 | Me | OEt | H | H | CF$_3$ | N | |
| 1.75 | Me | OEt | H | Me | CF$_3$ | N | |
| 1.76 | Me | OEt | H | Me | CF$_3$ | N | |
| 1.77 | Me | OEt | Me | Me | CF$_3$ | CH | |
| 1.78 | Me | OEt | H | Me | CH$_2$CF$_3$ | CMe | |
| 1.79 | Me | CN | H | H | CH$_2$CF$_3$ | N | |
| 1.80 | Me | CN | H | Me | CF$_3$ | N | |
| 1.81 | Me | CN | Me | H | CF$_3$ | CH | |
| 1.82 | Me | CN | Me | Me | CF$_3$ | CMe | |
| 1.83 | Me | CHO | H | H | CH$_2$CF$_3$ | N | |
| 1.84 | Me | CHO | H | Me | CF$_3$ | CH | |
| 1.85 | Me | CHO | Me | H | CF$_3$ | N | |
| 1.86 | Me | CHO | Me | Me | CF$_3$ | CMe | |
| 1.87 | Me | Vinyl | H | H | CH$_2$CF$_3$ | N | |
| 1.88 | Me | Vinyl | H | Me | CF$_3$ | CH | |
| 1.89 | Me | Vinyl | Me | H | CF$_3$ | N | |
| 1.90 | Me | Vinyl | Me | Me | CF$_3$ | CMe | |
| 1.91 | Me | Ethynyl | H | H | CH$_2$CF$_3$ | N | |
| 1.92 | Me | Ethynyl | H | Me | CF$_3$ | CH | |
| 1.93 | Me | Ethynyl | Me | H | CF$_3$ | N | |
| 1.94 | Me | Ethynyl | Me | Me | CF$_3$ | CMe | |
| 1.95 | Et | H | H | H | Cl | N | |
| 1.96 | Et | H | Me | Me | F | N | |
| 1.97 | Et | H | H | Me | CN | N | |
| 1.98 | Et | H | H | H | SCF$_3$ | CH | |
| 1.99 | Et | H | Me | H | OCF$_3$ | CMe | |
| 1.100 | Et | H | Me | Me | Br | CCl | |
| 1.101 | Et | H | H | Me | OCF$_3$ | CF | |
| 1.102 | Et | Me | H | H | CF$_3$ | N | |
| 1.103 | Et | Me | H | H | OCF$_2$H | N | |

TABLE 1-continued

Compounds of the formula (I) according to the invention in which the substituents and symbols are defined as follows:

A = A6     R⁶ = H

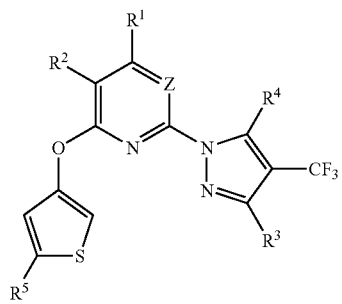

(Ia)

| No. | R¹ | R² | R³ | R⁴ | R⁵ | Z | Physical data |
|---|---|---|---|---|---|---|---|
| 1.104 | Et | Me | H | Me | CN | N | |
| 1.105 | Et | Me | Me | Me | Br | CH | |
| 1.106 | Et | Me | Me | Me | OCF$_3$ | CMe | |
| 1.107 | Et | Me | H | Me | CF$_3$ | CCl | |
| 1.108 | Et | Me | Me | H | OCF$_2$H | CF | |
| 1.109 | Et | Et | H | H | CF$_3$ | N | |
| 1.110 | Et | Et | H | H | OCF$_2$H | N | |
| 1.111 | Et | Et | H | Me | CN | N | |
| 1.112 | Et | Et | Me | Me | Br | CH | |
| 1.113 | Et | Et | Me | Me | OCF$_3$ | CMe | |
| 1.114 | Et | Et | H | Me | CF$_3$ | CCl | |
| 1.115 | Et | Et | Me | H | OCF$_2$H | CF | |
| 1.116 | Et | OMe | H | H | CF$_3$ | N | |
| 1.117 | Et | OMe | H | Me | CN | N | |
| 1.118 | Et | OMe | H | Me | CF$_3$ | N | |
| 1.119 | Et | OMe | Me | Me | CF$_3$ | CH | |
| 1.120 | Et | OMe | H | Me | CF$_3$ | CMe | |
| 1.121 | Et | OEt | H | H | CF$_3$ | N | |
| 1.122 | Et | OEt | H | Me | CF$_3$ | N | |
| 1.123 | Et | OEt | H | Me | CF$_3$ | N | |
| 1.124 | Et | OEt | Me | Me | CF$_3$ | CH | |
| 1.125 | Et | OEt | H | Me | CH$_2$CF$_3$ | CMe | |
| 1.126 | Et | CN | H | H | CH$_2$CF$_3$ | N | |
| 1.127 | Et | CN | H | Me | CF$_3$ | N | |
| 1.128 | Et | CN | Me | H | CF$_3$ | CH | |
| 1.129 | Et | CN | Me | Me | CF$_3$ | CMe | |
| 1.130 | Et | CHO | H | H | CH$_2$CF$_3$ | N | |
| 1.131 | Et | CHO | H | Me | CF$_3$ | CH | |
| 1.132 | Et | CHO | Me | H | CF$_3$ | N | |
| 1.133 | Et | CHO | Me | Me | CF$_3$ | CMe | |
| 1.134 | Et | Vinyl | H | H | CH$_2$CF$_3$ | N | |
| 1.135 | Et | Vinyl | H | Me | CF$_3$ | CH | |
| 1.136 | Et | Vinyl | Me | H | CF$_3$ | N | |
| 1.137 | Et | Vinyl | Me | Me | CF$_3$ | CMe | |
| 1.138 | Et | Ethynyl | H | H | CH$_2$CF$_3$ | N | |
| 1.139 | Et | Ethynyl | H | Me | CF$_3$ | CH | |
| 1.140 | Et | Ethynyl | Me | H | CF$_3$ | N | |
| 1.141 | Et | Ethynyl | Me | Me | CF$_3$ | CMe | |
| 1.142 | F | H | H | H | Cl | N | |
| 1.143 | Cl | H | Me | Me | F | N | |
| 1.144 | Br | H | H | Me | CN | N | |
| 1.145 | F | H | H | H | SCF$_3$ | CH | |
| 1.146 | Cl | H | Me | H | OCF$_3$ | CMe | |
| 1.147 | F | H | Me | Me | Br | CCl | |
| 1.148 | Cl | H | H | Me | OCF$_3$ | CF | |
| 1.149 | F | Me | H | H | CF$_3$ | N | |
| 1.150 | Cl | Me | H | H | OCF$_2$H | N | |
| 1.151 | Br | Me | H | Me | CN | N | |
| 1.152 | F | Me | Me | Me | Br | CH | |
| 1.153 | Cl | Me | Me | Me | OCF$_3$ | CMe | |
| 1.154 | Br | Me | H | Me | CF$_3$ | CCl | |

TABLE 1-continued

Compounds of the formula (I) according to the invention in which the substituents and symbols are defined as follows:

A = A6    R⁶ = H

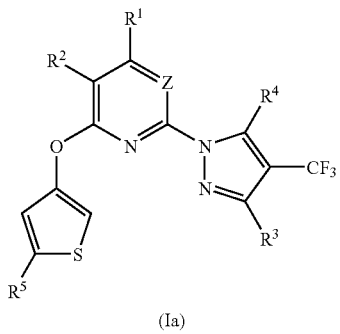

(Ia)

| No. | R¹ | R² | R³ | R⁴ | R⁵ | Z | Physical data |
|---|---|---|---|---|---|---|---|
| 1.155 | Br | Me | Me | H | OCF₂H | CF | |
| 1.156 | F | Et | H | H | CF₃ | N | |
| 1.157 | Cl | Et | H | H | OCF₂H | N | |
| 1.158 | F | Et | H | Me | CN | N | |
| 1.159 | Cl | Et | Me | Me | Br | CH | |
| 1.160 | F | Et | Me | Me | OCF₃ | CMe | |
| 1.161 | Cl | Et | H | Me | CF₃ | CCl | |
| 1.162 | F | Et | Me | H | OCF₂H | CF | |
| 1.163 | Cl | OMe | H | H | CF₃ | N | |
| 1.164 | F | OMe | H | Me | CN | N | |
| 1.165 | Cl | OMe | H | Me | CF₃ | N | |
| 1.166 | Br | OMe | Me | Me | CF₃ | CH | |
| 1.167 | F | OMe | H | Me | CF₃ | CMe | |
| 1.168 | Cl | OEt | H | H | CF₃ | N | |
| 1.169 | F | OEt | H | Me | CF₃ | N | |
| 1.170 | Cl | OEt | H | Me | CF₃ | N | |
| 1.171 | F | OEt | Me | Me | CF₃ | CH | |
| 1.172 | Cl | OEt | H | Me | CH₂CF₃ | CMe | |
| 1.173 | F | CN | H | H | CH₂CF₃ | N | |
| 1.174 | Cl | CN | H | Me | CF₃ | N | |
| 1.175 | F | CN | Me | H | CF₃ | CH | |
| 1.176 | Cl | CN | Me | Me | CF₃ | CMe | |
| 1.177 | F | CHO | H | H | CH₂CF₃ | N | |
| 1.178 | Cl | CHO | H | Me | CF₃ | CH | |
| 1.179 | Br | CHO | Me | H | CF₃ | N | |
| 1.180 | F | CHO | Me | Me | CF₃ | CMe | |
| 1.181 | Cl | Vinyl | H | H | CH₂CF₃ | N | |
| 1.182 | Br | Vinyl | H | Me | CF₃ | CH | |
| 1.183 | F | Vinyl | Me | H | CF₃ | N | |
| 1.184 | Cl | Vinyl | Me | Me | CF₃ | CMe | |
| 1.185 | Br | Ethynyl | H | H | CH₂CF₃ | N | |
| 1.186 | F | Ethynyl | H | Me | CF₃ | CH | |
| 1.187 | Cl | Ethynyl | Me | H | CF₃ | N | |
| 1.188 | Br | Ethynyl | Me | Me | CF₃ | CMe | |
| 1.189 | H | Cl | H | H | CF₃ | N | m.p. 78–80° C. |
| 1.190 | H | Me | Me | H | CF₃ | N | m.p. 99–101° C. |
| 1.191 | H | Me | H | Me | CF₃ | N | ¹H-NMR [CDCl₃]: 2.38 (s, 3H); 2.40 (s, 3H); 7.40 (m, 2H); 7.82 (s, 1H); 8.57 (s, 1H) |
| 1.192 | H | H | H | H | CF₃ | N | m.p. 48–50° C. |
| 1.193 | Me | H | H | H | CF₃ | N | ¹H-NMR [CDCl₃]: 2.60 (s, 3H); 6.75 (s, 1H); 7.41 (m, 1H); 7.48 (m, 1H); 7.98 (s, 1H); 8.62 (s, 1H) |
| 1.194 | H | Et | Me | H | CF₃ | N | |
| 1.195 | H | Me | Et | H | CF₃ | N | |

TABLE 2

Compounds of the formula (I) according to the invention in with the substituents and symbols are defined as follows:

A = A7   R⁶ = H

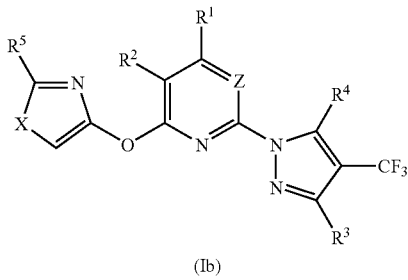

(Ib)

| No. | R¹ | R² | R³ | R⁴ | R⁵ | X | Z | Physical data |
|---|---|---|---|---|---|---|---|---|
| 2.1 | Cl | Me | H | H | CH₂CF₃ | O | N | |
| 2.2 | Cl | Me | H | Me | CH₂CF₃ | O | N | |
| 2.3 | F | Me | H | Me | CH₂CF₃ | S | CH | |
| 2.4 | H | Me | Me | H | CF₃ | O | CCl | |
| 2.5 | H | Et | Me | H | SMe | O | CMe | |
| 2.6 | H | Et | Cl | H | CF₃ | S | CF | |
| 2.7 | H | OMe | F | H | OCF₃ | O | N | |
| 2.8 | H | OMe | F | H | Cl | S | N | |
| 2.9 | H | OEt | Cl | H | CF₃ | O | CH | |
| 2.10 | H | OEt | F | H | OCF₃ | S | CCl | |
| 2.11 | Me | CHO | H | OMe | CHF₂ | S | CMe | |
| 2.12 | Me | CHO | H | OMe | CHF₂ | O | N | |
| 2.13 | Et | H | H | H | CHF₂ | S | N | |
| 2.14 | F | H | H | H | CH₂F | S | CH | |
| 2.15 | H | CN | H | H | CF₃ | O | CCl | |
| 2.16 | H | CN | OMe | H | CF₃ | O | N | |
| 2.17 | H | Vinyl | OMe | H | SMe | S | N | |
| 2.18 | Me | Vinyl | H | H | CH₂CF₃ | S | CH | |
| 2.19 | Me | Ethynyl | H | H | CH₂CF₃ | O | CCl | |
| 2.20 | Et | Ethynyl | H | H | CHF₂ | O | N | |

TABLE 3

Compounds of the formula (I) according to the invention in which the substituents and symbols are defined as follows:

A = A8   R⁶ = H

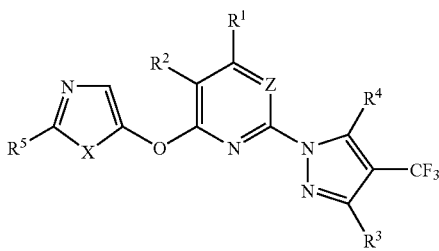

(Ic)

| No. | R¹ | R² | R³ | R⁴ | R⁵ | X | Z | Physical data |
|---|---|---|---|---|---|---|---|---|
| 3.1 | Cl | Me | H | H | CH₂CF₃ | O | N | |
| 3.2 | Cl | Me | H | Me | CH₂CF₃ | O | N | |
| 3.3 | F | Me | H | Me | CH₂CF₃ | S | CH | |
| 3.4 | H | Me | Me | H | CF₃ | O | CCl | |
| 3.5 | H | Et | Me | H | SMe | O | CMe | |
| 3.6 | H | Et | Cl | H | CF₃ | S | CF | |
| 3.7 | H | OMe | F | H | OCF₃ | O | N | |
| 3.8 | H | OMe | F | H | Cl | S | N | |
| 3.9 | H | OEt | Cl | H | CF₃ | O | CH | |
| 3.10 | H | OEt | F | H | OCF₃ | S | CCl | |
| 3.11 | Me | CHO | H | OMe | CHF₂ | S | CMe | |
| 3.12 | Me | CHO | H | OMe | CHF₂ | O | N | |
| 3.13 | Et | H | H | H | CHF₂ | S | N | |
| 3.14 | F | H | H | H | CH₂F | S | CH | |
| 3.15 | H | CN | H | H | CF₃ | O | CCl | |
| 3.16 | H | CN | OMe | H | CF₃ | O | N | |
| 3.17 | H | Vinyl | OMe | H | SMe | S | N | |
| 3.18 | Me | Vinyl | H | H | CH₂CF₃ | S | CH | |
| 3.19 | Me | Ethynyl | H | H | CH₂CF₃ | O | CCl | |
| 3.20 | Et | Ethynyl | H | H | CHF₂ | O | N | |

TABLE 4

Compounds of the formula (I) according to the invention in which the substituents and symbols are defined as follows:

A = A9   R⁶ = H

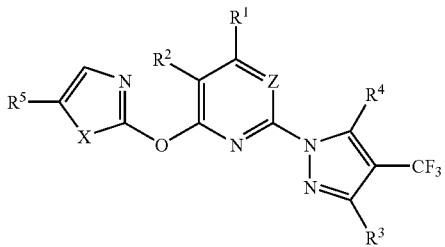

(Id)

| No. | R¹ | R² | R³ | R⁴ | R⁵ | X | Z | Physical data |
|---|---|---|---|---|---|---|---|---|
| 4.1 | Cl | Me | H | H | CH₂CF₃ | O | N | |
| 4.2 | Cl | Me | H | Me | CH₂CF₃ | O | N | |
| 4.3 | F | Me | H | Me | CH₂CF₃ | S | CH | |
| 4.4 | H | Me | Me | H | CF₃ | O | CCl | |
| 4.5 | H | Et | Me | H | SMe | O | CMe | |
| 4.6 | H | Et | Cl | H | CF₃ | S | CF | |
| 4.7 | H | OMe | F | H | OCF₃ | O | N | |
| 4.8 | H | OMe | F | H | Cl | S | N | |
| 4.9 | H | OEt | Cl | H | CF₃ | O | CH | |
| 4.10 | H | OEt | F | H | OCF₃ | S | CCl | |
| 4.11 | Me | CHO | H | OMe | CHF₂ | S | CMe | |
| 4.12 | Me | CHO | H | OMe | CHF₂ | O | N | |
| 4.13 | Et | H | H | H | CHF₂ | S | N | |
| 4.14 | F | H | H | H | CH₂F | S | CH | |
| 4.15 | H | CN | H | H | CF₃ | O | CCl | |
| 4.16 | H | CN | OMe | H | CF₃ | O | N | |
| 4.17 | H | Vinyl | OMe | H | SMe | S | N | |
| 4.18 | Me | Vinyl | H | H | CH₂CF₃ | S | CH | |
| 4.19 | Me | Ethynyl | H | H | CH₂CF₃ | O | CCl | |
| 4.20 | Et | Ethynyl | H | H | CHF₂ | O | N | |

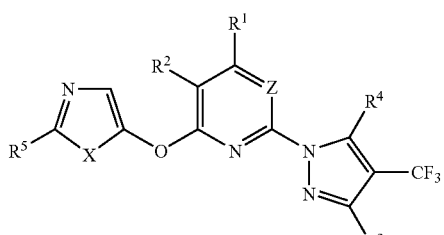

TABLE 5

Compounds of the formula (I) according to the invention in which the substituents and symbols are defined as follows:

A = A10    R⁶ = H

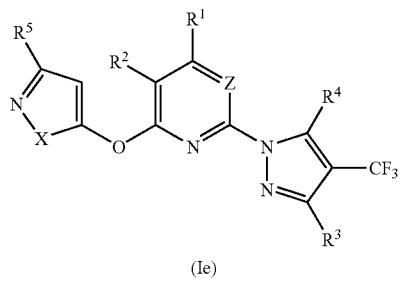

(Ie)

| No. | R¹ | R² | R³ | R⁴ | R⁵ | X | Z | Physical data |
|---|---|---|---|---|---|---|---|---|
| 5.1 | Cl | Me | H | H | CH$_2$CF$_3$ | O | N | |
| 5.2 | Cl | Me | H | Me | CH$_2$CF$_3$ | O | N | |
| 5.3 | F | Me | H | Me | CH$_2$CF$_3$ | S | CH | |
| 5.4 | H | Me | Me | H | CF$_3$ | O | CCl | |
| 5.5 | H | Et | Me | H | SMe | O | CMe | |
| 5.6 | H | Et | Cl | H | CF$_3$ | S | CF | |
| 5.7 | H | OMe | F | H | OCF$_3$ | O | N | |
| 5.8 | H | OMe | F | H | Cl | S | N | |
| 5.9 | H | OEt | Cl | H | CF$_3$ | O | CH | |
| 5.10 | H | OEt | F | H | OCF$_3$ | S | CCl | |
| 5.11 | Me | CHO | H | OMe | CHF$_2$ | S | CMe | |
| 5.12 | Me | CHO | H | OMe | CHF$_2$ | O | N | |
| 5.13 | Et | H | H | H | CHF$_2$ | S | N | |
| 5.14 | F | H | H | H | CH$_2$F | S | CH | |
| 5.15 | H | CN | H | H | CF$_3$ | O | CCl | |
| 5.16 | H | CN | OMe | H | CF$_3$ | O | N | |
| 5.17 | H | Vinyl | OMe | H | SMe | S | N | |
| 5.18 | Me | Vinyl | H | H | CH$_2$CF$_3$ | S | CH | |
| 5.19 | Me | Ethynyl | H | H | CH$_2$CF$_3$ | O | CCl | |
| 5.20 | Et | Ethynyl | H | H | CHF$_2$ | O | N | |

TABLE 6

Compounds of the formula (I) according to the invention in which the substituents and symbols are defined as follows:

A = A11    R⁶ = H

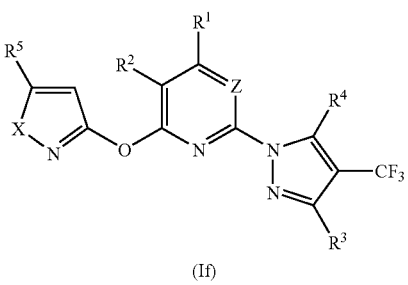

(If)

| No. | R¹ | R² | R³ | R⁴ | R⁵ | X | Z | Physical data |
|---|---|---|---|---|---|---|---|---|
| 6.1 | Cl | Me | H | H | CH$_2$CF$_3$ | O | N | |
| 6.2 | Cl | Me | H | Me | CH$_2$CF$_3$ | O | N | |
| 6.3 | F | Me | H | Me | CH$_2$CF$_3$ | S | CH | |
| 6.4 | H | Me | Me | H | CF$_3$ | O | CCl | |
| 6.5 | H | Et | Me | H | SMe | O | CMe | |
| 6.6 | H | Et | Cl | H | CF$_3$ | S | CF | |
| 6.7 | H | OMe | F | H | OCF$_3$ | O | N | |
| 6.8 | H | OMe | F | H | Cl | S | N | |
| 6.9 | H | OEt | Cl | H | CF$_3$ | O | CH | |
| 6.10 | H | OEt | F | H | OCF$_3$ | S | CCl | |
| 6.11 | Me | CHO | H | OMe | CHF$_2$ | S | CMe | |

TABLE 6-continued

Compounds of the formula (I) according to the invention in which the substituents and symbols are defined as follows:

A = A11    R⁶ = H

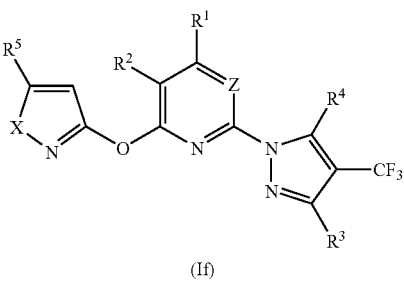

(If)

| No. | R¹ | R² | R³ | R⁴ | R⁵ | X | Z | Physical data |
|---|---|---|---|---|---|---|---|---|
| 6.12 | Me | CHO | H | OMe | CHF$_2$ | O | N | |
| 6.13 | Et | H | H | H | CHF$_2$ | S | N | |
| 6.14 | F | H | H | H | CH$_2$F | S | CH | |
| 6.15 | H | CN | H | H | CF$_3$ | O | CCl | |
| 6.16 | H | CN | OMe | H | CF$_3$ | O | N | |
| 6.17 | H | Vinyl | OMe | H | SMe | S | N | |
| 6.18 | Me | Vinyl | H | H | CH$_2$CF$_3$ | S | CH | |
| 6.19 | Me | Ethynyl | H | H | CH$_2$CF$_3$ | O | CCl | |
| 6.20 | Et | Ethynyl | H | H | CHF$_2$ | O | N | |

TABLE 7

Compounds of the formula (I) according to the invention in which the substituents and symbols are defined as follows:

A = A12

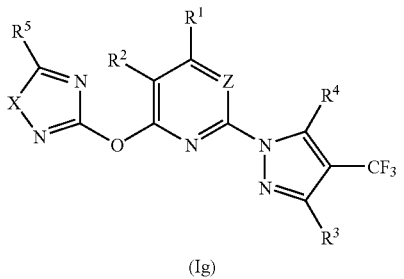

(Ig)

| No. | R¹ | R² | R³ | R⁴ | R⁵ | X | Z | Physical data |
|---|---|---|---|---|---|---|---|---|
| 7.1 | Cl | Me | H | H | CH$_2$CF$_3$ | O | N | |
| 7.2 | Cl | Me | H | Me | CH$_2$CF$_3$ | O | N | |
| 7.3 | F | Me | H | Me | CH$_2$CF$_3$ | S | CH | |
| 7.4 | H | Me | Me | H | CF$_3$ | O | CCl | |
| 7.5 | H | Et | Me | H | SMe | O | CMe | |
| 7.7 | H | Et | Cl | H | CF$_3$ | S | CF | |
| 7.7 | H | OMe | F | H | OCF$_3$ | O | N | |
| 7.8 | H | OMe | F | H | Cl | S | N | |
| 7.9 | H | OEt | Cl | H | CF$_3$ | O | CH | |
| 7.10 | H | OEt | F | H | OCF$_3$ | S | CCl | |
| 7.11 | Me | CHO | H | OMe | CHF$_2$ | S | CMe | |
| 7.12 | Me | CHO | H | OMe | CHF$_2$ | O | N | |
| 7.13 | Et | H | H | H | CHF$_2$ | S | N | |
| 7.14 | F | H | H | H | CH$_2$F | S | CH | |
| 7.15 | H | CN | H | H | CF$_3$ | O | CCl | |
| 7.17 | H | CN | OMe | H | CF$_3$ | O | N | |
| 7.17 | H | Vinyl | OMe | H | SMe | S | N | |
| 7.18 | Me | Vinyl | H | H | CH$_2$CF$_3$ | S | CH | |
| 7.19 | Me | Ethynyl | H | H | CH$_2$CF$_3$ | O | CCl | |
| 7.20 | Et | Ethynyl | H | H | CHF$_2$ | O | N | |

TABLE 8

Compounds of the formula (I) according to the invention in which the substituents and symbols are defined as follows:

A = A13

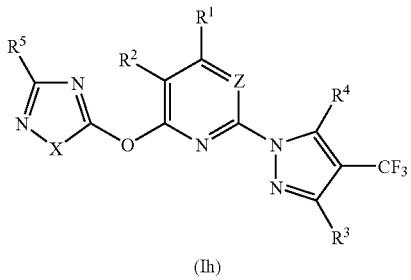

(Ih)

| No. | R¹ | R² | R³ | R⁴ | R⁵ | X | Z | Physical data |
|---|---|---|---|---|---|---|---|---|
| 8.1 | Cl | Me | H | H | $CH_2CF_3$ | O | N | |
| 8.2 | Cl | Me | H | Me | $CH_2CF_3$ | O | N | |
| 8.3 | F | Me | H | Me | $CH_2CF_3$ | S | CH | |
| 8.4 | H | Me | Me | H | $CF_3$ | O | CCl | |
| 8.5 | H | Et | Me | H | SMe | O | CMe | |
| 8.6 | H | Et | Cl | H | $CF_3$ | S | CF | |
| 8.7 | H | OMe | F | H | $OCF_3$ | O | N | |
| 8.8 | H | OMe | F | H | Cl | S | N | |
| 8.9 | H | OEt | Cl | H | $CF_3$ | O | CH | |
| 8.10 | H | OEt | F | H | $OCF_3$ | S | CCl | |
| 8.11 | Me | CHO | H | OMe | $CHF_2$ | S | CMe | |
| 8.12 | Me | CHO | H | OMe | $CHF_2$ | O | N | |
| 8.13 | Et | H | H | H | $CHF_2$ | S | N | |
| 8.14 | F | H | H | H | $CH_2F$ | S | CH | |
| 8.15 | H | CN | H | H | $CF_3$ | O | CCl | |
| 8.16 | H | CN | OMe | H | $CF_3$ | O | N | |
| 8.17 | H | Vinyl | OMe | H | SMe | S | N | |
| 8.18 | Me | Vinyl | H | H | $CH_2CF_3$ | S | CH | |
| 8.19 | Me | Ethynyl | H | H | $CH_2CF_3$ | O | CCl | |
| 8.20 | Et | Ethynyl | H | H | $CHF_2$ | O | N | |

TABLE 9

Compounds of the formula (I) according to the invention in which the substituents and symbols are defined as follows:

A = A14

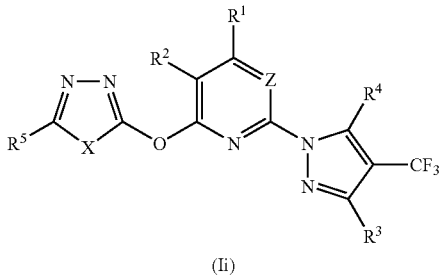

(Ii)

| No. | R¹ | R² | R³ | R⁴ | R⁵ | X | Z | Physical data |
|---|---|---|---|---|---|---|---|---|
| 9.1 | Cl | Me | H | H | $CH_2CF_3$ | O | N | |
| 9.2 | Cl | Me | H | Me | $CH_2CF_3$ | O | N | |
| 9.3 | F | Me | H | Me | $CH_2CF_3$ | S | CH | |
| 9.4 | H | Me | Me | H | $CF_3$ | O | CCl | |
| 9.5 | H | Et | Me | H | SMe | O | CMe | |
| 9.6 | H | Et | Cl | H | $CF_3$ | S | CF | |
| 9.7 | H | OMe | F | H | $OCF_3$ | O | N | |
| 9.8 | H | OMe | F | H | Cl | S | N | |
| 9.9 | H | OEt | Cl | H | $CF_3$ | O | CH | |
| 9.10 | H | OEt | F | H | $OCF_3$ | S | CCl | |
| 9.11 | Me | CHO | H | OMe | $CHF_2$ | S | CMe | |

TABLE 9-continued

Compounds of the formula (I) according to the invention in which the substituents and symbols are defined as follows:

A = A14

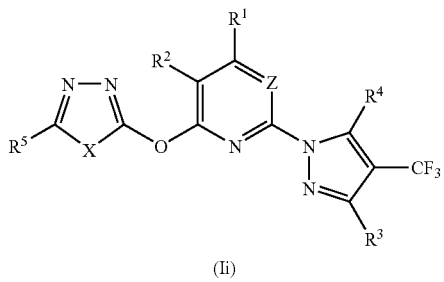

(Ii)

| No. | R¹ | R² | R³ | R⁴ | R⁵ | X | Z | Physical data |
|---|---|---|---|---|---|---|---|---|
| 9.12 | Me | CHO | H | OMe | $CHF_2$ | O | N | |
| 9.13 | Et | H | H | H | $CHF_2$ | S | N | |
| 9.14 | F | H | H | H | $CH_2F$ | S | CH | |
| 9.15 | H | CN | H | H | $CF_3$ | O | CCl | |
| 9.16 | H | CN | OMe | H | $CF_3$ | O | N | |
| 9.17 | H | Vinyl | OMe | H | SMe | S | N | |
| 9.18 | Me | Vinyl | H | H | $CH_2CF_3$ | S | CH | |
| 9.19 | Me | Ethynyl | H | H | $CH_2CF_3$ | O | CCl | |
| 9.20 | Et | Ethynyl | H | H | $CHF_2$ | O | N | |

TABLE 10

Compounds of the formula (I) according to the invention in which the substituents and symbols are defined as follows:

A = A15    R⁶ = H

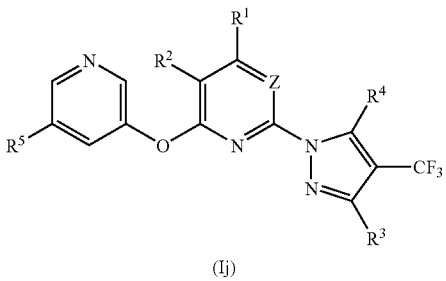

(Ij)

| No. | R¹ | R² | R³ | R⁴ | R⁵ | X | Z | Physical data |
|---|---|---|---|---|---|---|---|---|
| 10.1 | Cl | Me | H | H | $CH_2CF_3$ | O | N | |
| 10.2 | Cl | Me | H | Me | $CH_2CF_3$ | O | N | |
| 10.3 | F | Me | H | Me | $CH_2CF_3$ | S | CH | |
| 10.4 | H | Me | Me | H | $CF_3$ | O | CCl | |
| 10.5 | H | Et | Me | H | SMe | O | CMe | |
| 10.6 | H | Et | Cl | H | $CF_3$ | S | CF | |
| 10.7 | H | OMe | F | H | $OCF_3$ | O | N | |
| 10.8 | H | OMe | F | H | Cl | S | N | |
| 10.9 | H | OEt | Cl | H | $CF_3$ | O | CH | |
| 10.10 | H | OEt | F | H | $OCF_3$ | S | CCl | |
| 10.11 | Me | CHO | H | OMe | $CHF_2$ | S | CMe | |
| 10.12 | Me | CHO | H | OMe | $CHF_2$ | O | N | |
| 10.13 | Et | H | H | H | $CHF_2$ | S | N | |
| 10.14 | F | H | H | H | $CH_2F$ | S | CH | |
| 10.15 | H | CN | H | H | $CF_3$ | O | CCl | |
| 10.16 | H | CN | OMe | H | $CF_3$ | O | N | |
| 10.17 | H | Vinyl | OMe | H | SMe | S | N | |
| 10.18 | Me | Vinyl | H | H | $CH_2CF_3$ | S | CH | |
| 10.19 | Me | Ethynyl | H | H | $CH_2CF_3$ | O | CCl | |
| 10.20 | Et | Ethynyl | H | H | $CHF_2$ | O | N | |

B. FORMULATION EXAMPLES

1. Dust

A dust is obtained by mixing 10 parts by weight of a compound of the formula (I) and 90 parts by weight of talc as inert substance and comminuting the mixture in a hammer mill.

2. Dispersible Powder

A wettable powder which is readily dispersible in water is obtained by mixing 25 parts by weight of a compound of the formula (I), 64 parts by weight of kaolin-containing quartz as inert material, 10 parts by weight of potassium lignin-sulfonate and 1 part by weight of sodium oleoylmethyltauride as wetter and dispersant, and grinding the mixture in a pinned-disk mill.

3. Dispersion Concentrate

A dispersion concentrate which is readily dispersible in water is obtained by mixing 20 parts by weight of a compound of the formula (I), 6 parts by weight of alkylphenol polyglycol ether (®Triton X 207), 3 parts by weight of isotridecanol polyglycol ether (8 EO) and 71 parts by weight of paraffinic mineral oil (boiling range for example approx. 255 to above 277° C.), and grinding the mixture in a ball mill to a fineness of below 5 microns.

4. Emulsifiable Concentrate

An emulsifiable concentrate is obtained from 15 parts by weight of a compound of the formula (I), 75 parts by weight of cyclohexanone as solvent and 10 parts by weight of oxethylated nonylphenol as emulsifier.

5. Water-Dispersible Granules

Water-dispersible granules are obtained by mixing 75 parts by weight of a compound of the formula (I),
10" calcium ligninsulfonate,
5" sodium lauryl sulfate,
3" polyvinyl alcohol and
7" kaolin, grinding the mixture in a pinned-disk mill and granulating the powder in a fluidized bed by spraying on water as granulation liquid.

Water-dispersible granules are also obtained by homogenizing and precomminuting, in a colloid mill, 25 parts by weight of a compound of the formula (I),
5" sodium 2,2'-dinaphthylmethane-6,6'-disulfonate,
2" sodium oleoylmethyltauride,
1" polyvinyl alcohol,
17" calcium carbonate and
50" water, subsequently grinding the mixture in a bead mill, and atomizing and drying the resulting suspension in a spray tower by means of a single-substance nozzle.

C. BIOLOGICAL EXAMPLES

1. Weed plant herbicidal activity and crop plant tolerance, pre-emergence Seeds of monocot and dicot weed plants and of crop plants are placed in sandy loam soil in cardboard pots and are covered with soil. The compounds of the invention, formulated as wettable powders or emulsifiable concentrates, are then applied as an aqueous suspension or emulsion, respectively, in different dosages to the surface of the covering soil at an application rate of 600 to 800 l of water per ha (converted). Following treatment, the pots are placed in a greenhouse and kept under good growth conditions for the weeds. Visual scoring of the plant damage or emergence damage is made after the experimental plants have emerged, after an experimental period of 3 to 4 weeks, in comparison with untreated controls. In this case, for example, the compounds of the invention from Example No. 1.22 at a rate of 20 g of active substance per hectare displays an activity of at least 80% against *Amaranthus retroflexus, Avena fatua, Agropyrons repens, Alopecurus myosuroides, Digitaria sanguinalis, Galium aparine, Lolium multiflorum, Setaria viridis, Sorghum halepense* and *Veronica persica*. At the same application rate this compound of the invention causes no damage to the crop plants *Oryza sativa* (rice) or *Zea mays* (maize).

2. Weed plant herbicidal activity and crop plant tolerance, post-emergence Seeds of monocot and dicot weed plants and of crop plants are placed in sandy loam in cardboard pots, covered with soil, and grown under good growth conditions in a greenhouse. Two to three weeks after sowing, the experimental plants are treated at the three-leaf stage. The compounds of the invention, formulated as wettable powders or as emulsifiable concentrates, are sprayed at different dosages onto the surface of the green parts of the plants at an application rate of 600 to 800 l of water per ha (converted). After the experimental plants have stood in the greenhouse for 3 to 4 weeks under optimum growth conditions, the activity of the compounds is scored. In this case, for example, at a rate of 80 g of active substance per hectare, the compound from Example No. 1.22 displays an activity of at least 90% against *Chenopodium album, Digitaria sanguinalis, Matricaria inodora, Pharbitis purpureum,* and *Veronica persica*. At the same application rate this compound of the invention causes no damage to the crop plant *Oryza sativa* (rice) and 20% damage to *Triticum aestivum* (wheat).

What is claimed is:

1. A compound of the formula (I) or an N-oxide or salt thereof,

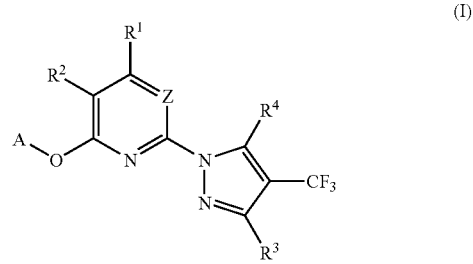

in which the radicals and indices have the following definitions:

$Z$ is $CR^8$;

$A$ is

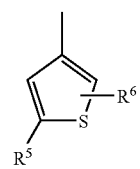

A6

$R_1$ and $R_2$ independently are each hydrogen, halogen, cyano, isocyano, OH, COOR$^{10}$, COR$^{10}$, CH$_2$OH, CH$_2$SH, CH$_2$NH$_2$, NO$_2$, (C$_1$–C$_4$)-alkyl, halo-(C$_1$–C$_4$)-alkyl, (C$_3$–C$_6$)-cycloalkyl, (C$_1$–C$_4$)-alkoxy, halogen-(C$_1$–C$_4$)-alkoxy, (C$_1$–C$_2$)-alkoxy-(C$_1$–C$_2$)-alkyl, (C$_2$–C$_4$)-alkenyl, (C$_2$–C$_4$)-alkynyl, (C$_3$–C$_4$)-alkenyloxy, (C$_3$–C$_4$)-alkynyloxy, (C$_1$–C$_2$)-alkylthio-(C$_1$–C$_2$)-alkyl, S(O)$_n$R$^9$, (C$_1$–C$_2$)-alkylsulfonyl-(C$_1$–C$_2$)-alkyl, NH$_2$, (C$_1$–C$_4$)-alkyl-NH, (C$_1$–C$_3$)-alkyl-CO—NH, (C$_1$–C$_4$)-alkyl-SO$_2$NH or di-(C$_1$–C$_4$)-alkylamino;

$R_3$ and $R_4$ independently are each hydrogen, halogen, cyano, (C$_1$–C$_4$)-alkyl, halo-(C$_1$–C$_4$)-alkyl, (C$_1$–C$_4$)-alkoxy or halo-(C$_1$–C$_4$)-alkoxy;

$R^5$ is halogen, cyano, (C$_1$–C$_4$)-alkyl, halo-(C$_1$–C$_4$)-alkyl, (C$_1$–C$_4$)-alkoxy, halo-(C$_1$–C$_4$)-alkoxy, halo-(C$_1$–C$_4$)-alkylthio, (C$_3$–C$_5$)-cycloalkyl, halo-(C$_3$–C$_5$)-cycloalkyl, SF$_5$, S(O)$_n$R$^9$, (C$_2$–C$_4$)-alkenyl or (C$_2$–C$_4$)-alkynyl;

$R_6$ is hydrogen, halogen, cyano, (C$_1$–C$_4$)-alkyl, halo-(C$_1$–C$_4$)-alkyl, (C$_1$–C$_4$)-alkoxy, halo-(C$_1$–C$_4$)-alkoxy or S(O)$_n$R$^9$;

$R_8$ is hydrogen, halogen, cyano, (C$_1$–C$_4$)-alkyl, (C$_1$–C$_4$)-alkoxy, hydroxy, amino, (C$_1$–C$_4$)-alkylamino, (C$_1$–C$_3$)-alkylcarbonylamino, (C$_1$–C$_4$)-alkylsulfonylamino, di-(C$_1$–C$_4$)-alkylamino or S(O)$_n$R$^9$;

$R^9$ is hydrogen, (C$_1$–C$_4$)-alkyl or halo-(C$_1$–C$_4$)-alkyl;

$R^{10}$ is hydrogen or (C$_1$–C$_4$)alkyl; and n is 0, 1 or 2.

2. A compound of claim 1, wherein $R^8$ is H, CH$_3$, Cl or F.

3. A compound of claim 1, wherein $R^1$ is H, CH$_3$, CH$_2$CH$_3$, Cl, Br or F, $R^2$ is H, CH$_3$, OCH$_3$, OCH$_2$CH$_3$, CH$_2$CH$_3$, CN, CHO, vinyl, ethynyl, Cl, Br or F, $R^3$ is H, CH$_3$ or CH$_2$CH$_3$, $R^4$ is H, CH$_3$ or CH$_2$CH$_3$, $R^5$ is CN, CF$_3$, OCF$_3$, OCF$_2$H, Cl, Br, F, CH$_2$CF$_3$ or SCF$_3$, $R^6$ is H, and $R^8$ is H, CH$_3$, Cl or F.

* * * * *